United States Patent
Weinstein et al.

(10) Patent No.: US 10,136,833 B2
(45) Date of Patent: Nov. 27, 2018

(54) IMPLANTABLE RADIO-FREQUENCY SENSOR

(71) Applicant: ZOLL MEDICAL ISRAEL LTD., Kfar Saba (IL)

(72) Inventors: Uriel Weinstein, Mazkeret Batia (IL); Assaf Bernstein, Givat Nili (IL); Eyal Cohen, Ariel (IL); Dov Oppenheim, Jerusalem (IL); Moshe Mosesko, Kadima (IL)

(73) Assignee: ZOLL MEDICAL ISRAEL, LTD., Kfar Saba (IL)

( * ) Notice: Subject to any disclaimer, the term of this patent is extended or adjusted under 35 U.S.C. 154(b) by 0 days.

(21) Appl. No.: 15/589,813

(22) Filed: May 8, 2017

(65) Prior Publication Data
US 2017/0238966 A1 Aug. 24, 2017

Related U.S. Application Data

(62) Division of application No. 13/811,210, filed as application No. PCT/IB2011/053244 on Jul. 21, 2011, now abandoned.
(Continued)

(51) Int. Cl.
*A61B 5/00* (2006.01)
*A61B 5/053* (2006.01)
(Continued)

(52) U.S. Cl.
CPC ............ *A61B 5/0538* (2013.01); *A61B 1/313* (2013.01); *A61B 5/0028* (2013.01);
(Continued)

(58) Field of Classification Search
CPC ................ A61B 17/3468; A61B 1/313; A61B 2560/0219; A61B 2562/0214;
(Continued)

(56) References Cited

U.S. PATENT DOCUMENTS

| | | | |
|---|---|---|---|
| 4,240,445 A | 12/1980 | Durney et al. | |
| 4,344,440 A | 8/1982 | Aaby et al. | |

(Continued)

FOREIGN PATENT DOCUMENTS

| | | |
|---|---|---|
| CN | 101032400 A | 9/2007 |
| CN | 101516437 A | 8/2009 |

(Continued)

OTHER PUBLICATIONS

Alekseev, S. I., et al. "Human Skin permittivity determined by millimeter wave reflection measurements", Bioelectromagnetics, vol. 28, No. 5, Jul. 1, 2007, pp. 331-339.
(Continued)

*Primary Examiner* — Ruth S Smith
(74) *Attorney, Agent, or Firm* — Cooley LLP

(57) ABSTRACT

A diagnostic apparatus comprising a sealed case, a first antenna and a second antenna and processing circuitry are disclosed herein. In some embodiments, the sealed case includes a biocompatible material and is configured for implantation within a body of a patient. Further, each one of the first antenna and the second antenna are configured to be implanted in the body in proximity to a target tissue, generate and transmit radio frequency (RF) electromagnetic waves through the target tissue to the other antenna, and output a signal in response to RF waves received from the other antenna. In addition, the processing circuitry can be contained within the case and is configured to receive and process the signal from each antenna so as to derive and output an indication of a characteristic of the target tissue.

19 Claims, 7 Drawing Sheets

Related U.S. Application Data

(60) Provisional application No. 61/366,173, filed on Jul. 21, 2010.

(51) Int. Cl.
*A61B 5/0215* (2006.01)
*A61B 5/042* (2006.01)
*A61B 5/05* (2006.01)
*A61N 1/375* (2006.01)
*A61B 5/0205* (2006.01)
*A61B 1/313* (2006.01)
*A61B 5/07* (2006.01)
*A61B 5/08* (2006.01)
*A61B 17/34* (2006.01)
*A61B 5/01* (2006.01)
*A61B 5/145* (2006.01)
*A61N 1/365* (2006.01)
*A61N 1/37* (2006.01)
*A61N 1/372* (2006.01)

(52) U.S. Cl.
CPC .......... *A61B 5/0031* (2013.01); *A61B 5/0059* (2013.01); *A61B 5/0205* (2013.01); *A61B 5/0215* (2013.01); *A61B 5/0422* (2013.01); *A61B 5/05* (2013.01); *A61B 5/0537* (2013.01); *A61B 5/076* (2013.01); *A61B 5/0809* (2013.01); *A61B 5/416* (2013.01); *A61B 5/4244* (2013.01); *A61B 5/4552* (2013.01); *A61B 5/4875* (2013.01); *A61B 5/686* (2013.01); *A61B 5/6833* (2013.01); *A61B 5/72* (2013.01); *A61B 17/3468* (2013.01); *A61N 1/3756* (2013.01); *A61B 5/01* (2013.01); *A61B 5/14542* (2013.01); *A61B 2560/0219* (2013.01); *A61B 2562/0214* (2013.01); *A61B 2562/164* (2013.01); *A61N 1/36521* (2013.01); *A61N 1/3702* (2013.01); *A61N 1/37229* (2013.01)

(58) Field of Classification Search
CPC ............ A61B 2562/164; A61B 5/0028; A61B 5/0031; A61B 5/0059; A61B 5/01; A61B 5/0205; A61B 5/0215; A61B 5/0422; A61B 5/05; A61B 5/0537; A61B 5/0538; A61B 5/076; A61B 5/0809; A61B 5/14542; A61B 5/416; A61B 5/4244; A61B 5/4552; A61B 5/4875; A61B 5/6833; A61B 5/686; A61B 5/72; A61N 1/36521; A61N 1/3702; A61N 1/37229; A61N 1/3756
See application file for complete search history.

(56) References Cited

U.S. PATENT DOCUMENTS

| | | |
|---|---|---|
| 4,557,272 A | 12/1985 | Carr |
| 4,632,128 A | 12/1986 | Paglione et al. |
| 4,640,280 A | 2/1987 | Sterzer |
| 4,641,659 A | 2/1987 | Sepponen |
| 4,774,961 A | 10/1988 | Carr |
| 4,825,880 A | 5/1989 | Stauffer et al. |
| 4,926,868 A | 5/1990 | Larsen |
| 4,945,914 A | 8/1990 | Allen |
| 4,958,638 A | 9/1990 | Sharpe |
| 4,986,870 A | 1/1991 | Frohlich |
| 5,003,622 A | 3/1991 | Ma et al. |
| 5,109,855 A | 5/1992 | Guner |
| 5,394,882 A | 3/1995 | Mawhinney |
| 5,404,877 A | 4/1995 | Nolan |
| 5,474,574 A | 12/1995 | Payne et al. |
| 5,540,727 A | 7/1996 | Tockman et al. |
| 5,549,650 A | 8/1996 | Bornzin et al. |
| 5,668,555 A | 9/1997 | Starr |
| 5,704,355 A | 1/1998 | Bridges |
| 5,766,208 A | 6/1998 | McEwan |
| 5,807,257 A | 9/1998 | Bridges |
| 5,829,437 A | 11/1998 | Bridges |
| 5,841,288 A | 11/1998 | Meaney et al. |
| 5,865,177 A | 2/1999 | Segawa |
| 5,967,986 A | 10/1999 | Cimochowski et al. |
| 6,019,724 A | 2/2000 | Gronningsaeter et al. |
| 6,061,589 A | 5/2000 | Bridges et al. |
| 6,064,903 A | 5/2000 | Riechers et al. |
| 6,093,141 A | 7/2000 | Mosseri et al. |
| 6,144,344 A | 11/2000 | Kim |
| 6,193,669 B1 | 2/2001 | Degany et al. |
| 6,208,286 B1 | 3/2001 | Rostislavovich et al. |
| 6,233,479 B1 | 5/2001 | Haddad et al. |
| 6,267,723 B1 | 7/2001 | Matsumura et al. |
| 6,330,479 B1 | 12/2001 | Stauffer |
| 6,409,662 B1 | 6/2002 | Lloyd et al. |
| 6,454,711 B1 | 9/2002 | Haddad et al. |
| 6,480,733 B1 | 11/2002 | Turcott |
| 6,526,318 B1 | 2/2003 | Ansarinia |
| 6,592,518 B2 * | 7/2003 | Denker ................ A61B 5/0031 600/300 |
| 6,604,404 B2 | 8/2003 | Paltieli et al. |
| 6,729,336 B2 | 5/2004 | Da Silva et al. |
| 6,730,033 B2 | 5/2004 | Yao et al. |
| 6,755,856 B2 | 6/2004 | Fierens et al. |
| 6,933,811 B2 | 8/2005 | Enokihara et al. |
| 6,940,457 B2 | 9/2005 | Lee et al. |
| 7,020,508 B2 | 3/2006 | Stivoric et al. |
| 7,122,012 B2 | 10/2006 | Bouton et al. |
| 7,130,681 B2 | 10/2006 | Gebhardt et al. |
| 7,184,824 B2 | 2/2007 | Hashimshony |
| 7,191,000 B2 | 3/2007 | Zhu et al. |
| 7,197,356 B2 | 3/2007 | Carr |
| 7,266,407 B2 | 9/2007 | Li et al. |
| 7,267,651 B2 | 9/2007 | Nelson |
| 7,272,431 B2 | 9/2007 | McGrath |
| 7,280,863 B2 | 10/2007 | Shachar |
| 7,454,242 B2 | 11/2008 | Fear et al. |
| 7,474,918 B2 | 1/2009 | Frants et al. |
| 7,479,790 B2 | 1/2009 | Choi |
| 7,493,154 B2 | 2/2009 | Bonner et al. |
| 7,529,398 B2 | 5/2009 | Zwirn et al. |
| 7,570,063 B2 | 8/2009 | Van Veen et al. |
| 7,591,792 B2 | 9/2009 | Bouton |
| 7,697,972 B2 | 4/2010 | Verard et al. |
| 7,719,280 B2 | 5/2010 | Lagae et al. |
| 7,747,302 B2 | 6/2010 | Milledge et al. |
| 7,868,627 B2 | 1/2011 | Turkovskyi |
| 8,032,211 B2 | 10/2011 | Hashimshony et al. |
| 8,211,040 B2 | 7/2012 | Kojima et al. |
| 8,295,920 B2 | 10/2012 | Bouton et al. |
| 8,352,015 B2 | 1/2013 | Bernstein et al. |
| 8,473,054 B2 | 6/2013 | Pillai et al. |
| 8,682,399 B2 | 3/2014 | Rabu |
| 8,882,759 B2 | 11/2014 | Manley et al. |
| 8,938,292 B2 | 1/2015 | Hettrick et al. |
| 8,983,592 B2 | 3/2015 | Belalcazar |
| 8,989,837 B2 | 3/2015 | Weinstein et al. |
| 9,220,420 B2 | 12/2015 | Weinstein et al. |
| 9,265,438 B2 | 2/2016 | Weinstein et al. |
| 9,572,512 B2 | 2/2017 | Weinstein et al. |
| 9,629,561 B2 | 4/2017 | Weinstein et al. |
| 9,788,752 B2 | 10/2017 | Weinstein et al. |
| 2002/0032386 A1 | 3/2002 | Sackner et al. |
| 2002/0045836 A1 | 4/2002 | Alkawwas |
| 2002/0049394 A1 | 4/2002 | Roy et al. |
| 2002/0050954 A1 | 5/2002 | Jeong-Kun et al. |
| 2002/0147405 A1 | 10/2002 | Denker et al. |
| 2002/0151816 A1 | 10/2002 | Rich et al. |
| 2003/0036674 A1 | 2/2003 | Bouton |
| 2003/0036713 A1 | 2/2003 | Bouton et al. |
| 2003/0088180 A1 | 5/2003 | Van Veen et al. |
| 2003/0100815 A1 | 5/2003 | Da Silva et al. |
| 2003/0199770 A1 | 10/2003 | Chen et al. |

(56) References Cited

U.S. PATENT DOCUMENTS

| | | |
|---|---|---|
| 2003/0219598 A1 | 11/2003 | Sakurai |
| 2004/0015087 A1 | 1/2004 | Boric-Lubecke et al. |
| 2004/0073081 A1 | 4/2004 | Schramm |
| 2004/0077943 A1 | 4/2004 | Meaney et al. |
| 2004/0077952 A1 | 4/2004 | Rafter et al. |
| 2004/0249257 A1 | 12/2004 | Tupin et al. |
| 2004/0254457 A1 | 12/2004 | van der Weide |
| 2004/0261721 A1 | 12/2004 | Steger |
| 2005/0038503 A1 | 2/2005 | Greenhalgh et al. |
| 2005/0107693 A1 | 5/2005 | Fear et al. |
| 2005/0192488 A1 | 9/2005 | Bryenton |
| 2005/0245816 A1 | 11/2005 | Candidus et al. |
| 2006/0004269 A9 | 1/2006 | Caduff et al. |
| 2006/0009813 A1 | 1/2006 | Taylor et al. |
| 2006/0025661 A1 | 2/2006 | Sweeney et al. |
| 2006/0101917 A1 | 5/2006 | Merkel |
| 2006/0265034 A1 | 11/2006 | Aknine et al. |
| 2007/0016032 A1 | 1/2007 | Aknine |
| 2007/0016050 A1 | 1/2007 | Moehring et al. |
| 2007/0055123 A1 | 3/2007 | Takiguchi |
| 2007/0100385 A1 | 5/2007 | Rawat |
| 2007/0123770 A1 | 5/2007 | Bouton et al. |
| 2007/0123778 A1 | 5/2007 | Kantorovich |
| 2007/0135721 A1 | 6/2007 | Zdeblick |
| 2007/0152812 A1 | 7/2007 | Wong et al. |
| 2007/0156057 A1 | 7/2007 | Cho et al. |
| 2007/0162090 A1 | 7/2007 | Penner |
| 2007/0191733 A1 | 8/2007 | Gianchandani et al. |
| 2007/0263907 A1 | 11/2007 | McMakin et al. |
| 2008/0027313 A1 | 1/2008 | Shachar |
| 2008/0030284 A1 | 2/2008 | Tanaka et al. |
| 2008/0036668 A1 | 2/2008 | White et al. |
| 2008/0097199 A1 | 4/2008 | Mullen |
| 2008/0129511 A1 | 6/2008 | Yuen et al. |
| 2008/0167566 A1 | 7/2008 | Unver et al. |
| 2008/0169961 A1 | 7/2008 | Steinway et al. |
| 2008/0183247 A1 | 7/2008 | Harding |
| 2008/0200802 A1 | 8/2008 | Bahavaraju et al. |
| 2008/0224688 A1 | 9/2008 | Rubinsky et al. |
| 2008/0269589 A1 | 10/2008 | Thijs et al. |
| 2008/0283282 A1 | 11/2008 | Kawasaki et al. |
| 2008/0294036 A1 | 11/2008 | Hoi et al. |
| 2008/0316124 A1 | 12/2008 | Hook |
| 2008/0319301 A1 | 12/2008 | Busse |
| 2009/0021720 A1 | 1/2009 | Hecker |
| 2009/0048500 A1 | 2/2009 | Corn |
| 2009/0076350 A1 | 3/2009 | Bly et al. |
| 2009/0153412 A1 | 6/2009 | Chiang et al. |
| 2009/0187109 A1 | 7/2009 | Hashimshony |
| 2009/0203972 A1 | 8/2009 | Heneghan et al. |
| 2009/0227882 A1 | 9/2009 | Foo |
| 2009/0240132 A1 | 9/2009 | Friedman |
| 2009/0240133 A1 | 9/2009 | Friedman |
| 2009/0248450 A1 | 10/2009 | Fernandez |
| 2009/0281412 A1 | 11/2009 | Boyden et al. |
| 2009/0299175 A1 | 12/2009 | Bernstein et al. |
| 2009/0312615 A1 | 12/2009 | Caduff et al. |
| 2009/0322636 A1 | 12/2009 | Brigham et al. |
| 2010/0056907 A1 | 3/2010 | Rappaport et al. |
| 2010/0081895 A1 | 4/2010 | Zand |
| 2010/0106223 A1 | 4/2010 | Grevious |
| 2010/0152600 A1 | 6/2010 | Droitcour et al. |
| 2010/0256462 A1 | 10/2010 | Rappaport et al. |
| 2010/0265159 A1 | 10/2010 | Ando et al. |
| 2010/0312301 A1 | 12/2010 | Stahmann |
| 2010/0321253 A1 | 12/2010 | Vazquez et al. |
| 2010/0332173 A1 | 12/2010 | Watson et al. |
| 2011/0004076 A1 | 1/2011 | Janna et al. |
| 2011/0009754 A1 | 1/2011 | Wenzel et al. |
| 2011/0022325 A1 | 1/2011 | Craddock et al. |
| 2011/0040176 A1 | 2/2011 | Razansky et al. |
| 2011/0060215 A1 | 3/2011 | Tupin et al. |
| 2011/0068995 A1 | 3/2011 | Baliarda et al. |
| 2011/0125207 A1 | 5/2011 | Nabutovsky et al. |
| 2011/0130800 A1 | 6/2011 | Weinstein et al. |
| 2011/0257555 A1 | 10/2011 | Banet et al. |
| 2012/0029323 A1 | 2/2012 | Zhao |
| 2012/0065514 A1 | 3/2012 | Naghavi et al. |
| 2012/0098706 A1 | 4/2012 | Lin et al. |
| 2012/0104103 A1 | 5/2012 | Manzi |
| 2012/0330151 A1 | 12/2012 | Weinstein et al. |
| 2013/0041268 A1 | 2/2013 | Rimoldi et al. |
| 2013/0090566 A1 | 4/2013 | Muhlsteff et al. |
| 2013/0123614 A1 | 5/2013 | Bernstein et al. |
| 2013/0184573 A1 | 7/2013 | Pahlevan et al. |
| 2013/0190646 A1 | 7/2013 | Weinstein et al. |
| 2013/0225989 A1 | 8/2013 | Saroka et al. |
| 2013/0231550 A1 | 9/2013 | Weinstein et al. |
| 2013/0310700 A1 | 11/2013 | Wiard et al. |
| 2014/0081159 A1 | 3/2014 | Tao et al. |
| 2014/0163425 A1 | 6/2014 | Tran |
| 2015/0025333 A1 | 1/2015 | Weinstein et al. |
| 2015/0150477 A1 | 6/2015 | Weinstein et al. |
| 2015/0335310 A1 | 11/2015 | Bernstein et al. |
| 2016/0073924 A1 | 3/2016 | Weinstein et al. |
| 2016/0198976 A1 | 7/2016 | Weinstein et al. |
| 2016/0213321 A1 | 7/2016 | Weinstein et al. |
| 2016/0317054 A1 | 11/2016 | Weinstein et al. |
| 2017/0135598 A1 | 5/2017 | Weinstein et al. |

FOREIGN PATENT DOCUMENTS

| | | |
|---|---|---|
| DE | 10008886 | 9/2001 |
| EP | 1834588 A1 | 9/2007 |
| EP | 2506917 A1 | 10/2012 |
| JP | 10-137193 A | 5/1998 |
| JP | 2000-235006 A | 8/2000 |
| JP | 2001-525925 A | 12/2001 |
| JP | 2004-526488 A | 9/2004 |
| JP | 2006-208070 A | 8/2006 |
| JP | 2006-319767 A | 11/2006 |
| JP | 2007-061359 A | 3/2007 |
| JP | 2008-515548 A | 5/2008 |
| JP | 2008-148141 A | 6/2008 |
| JP | 2008-518706 A | 6/2008 |
| JP | 2008-530546 A | 7/2008 |
| JP | 2008-542759 A | 11/2008 |
| JP | 2009-514619 A | 4/2009 |
| JP | 2009-522034 A | 6/2009 |
| JP | 2010-512190 A | 4/2010 |
| JP | 2010-537766 A | 12/2010 |
| JP | 2011-507583 A | 3/2011 |
| JP | 2011-524213 A | 9/2011 |
| WO | WO 2003/009752 A2 | 2/2003 |
| WO | WO 2006/127719 A2 | 11/2006 |
| WO | WO 2006/130798 A2 | 12/2006 |
| WO | WO 2007/017861 A2 | 2/2007 |
| WO | WO 2008/070856 A2 | 6/2008 |
| WO | WO 2008/148040 A1 | 12/2008 |
| WO | WO 2009/031149 A2 | 3/2009 |
| WO | WO 2009/060182 A1 | 5/2009 |
| WO | WO 2009/081331 A1 | 7/2009 |
| WO | WO 2009/152625 A1 | 12/2009 |
| WO | WO 2011/067623 A1 | 6/2011 |
| WO | WO 2011/067685 A1 | 6/2011 |
| WO | WO 2011/141915 A2 | 11/2011 |
| WO | WO 2012/011065 A1 | 1/2012 |
| WO | WO 2012/011066 A1 | 1/2012 |
| WO | WO 2013/118121 A1 | 8/2013 |
| WO | WO 2013/121290 A2 | 8/2013 |
| WO | WO 2015/118544 A1 | 8/2015 |

OTHER PUBLICATIONS

Ascension Technology Corporation, "TrakSTAR Adds Versatility to Ascension's New Product Line: Desktop Model Joins driveBAY Tracker for Fast Guidance of Miniaturized Sensor", USA, Apr. 7, 2008.

Bell et al., "A Low-Profile Achimedean Spiral Antenna Using an EBG Ground Plane", IEEE Antennas and Wireless Propagation Letters 3, pp. 223-226 (2004).

(56) References Cited

OTHER PUBLICATIONS

Beyer-Enke et al., Intra-arterial Doppler flowmetry in the superficial femoral artery following angioplasty., 2000, European Radiology, vol. 10, No. 4, p. 642-649.
Claron Technology Inc., "MicronTracker 3: A New Generation of Optical Trackers", Canada, 2009.
Czum et al., "The Vascular Diagnostic Laboratory", The Heart & Vascular Institute Newsletter, vol. 1, USA, Winter, 2001.
Extended Search Report for European Application No. 11809360.8, dated Mar. 11, 2014.
Ghosh, et al., Immediate Evaluation of Angioplasty and Stenting Results in Supra-Aortic Arteries by Use of a Doppler-Tipped Guidewire, Aug. 2004, American Journal of Neuroradiology, vol. 25, p. 1172-1176.
Gentili et al., "A Versatile Microwave Plethysmograph for the Monitoring of Physiological Parameters", IEEE Transactions on Biomedical Engineering, IEEE Service Center, Pitscataway, NJ, US, vol. 49, No. 10, Oct. 1, 2002.
Haude et al., Intracoronary Doppler-and Quantitative Coronary Angiography-Derived Predictors of Major Adverse Cardiac Events After Stent Implantation, Mar. 6 2001, Circulation, vol. 103(9), p. 1212-1217.
Immersion Corporation, "Immersion Introduces New 3D Digitizing Product-MicroScribe G2; Faster Data Transfer, USB Compatibility, New Industrial Design", Press Release, San Jose, USA, Jul. 1, 2002.
International Preliminary Report on Patentability, dated Jan. 31, 2013, for International Application No. PCT/IB2011/053246, 22 pages.
International Preliminary Report on Patentability, dated Aug. 19, 2014 for International Application No. PCT/IB2013/000663 filed Feb. 15, 2013.
International Preliminary Report on Patentability, dated Jun. 5, 2012, for International Application No. PCT/IB2010/054861.
International Preliminary Report on Patentability, dated Jan. 22, 2013, for International Application No. PCT/IB2011/053244, 6 pages.
International Preliminary Report on Patentability, dated Jun. 5, 2012, for International Application No. PCT/IB2009/055438.
International Search Report and Written Opinion of the International Searching Authority, dated Dec. 2, 2011, for International Application No. PCT/IB2011/053244, 7 pages.
International Search Report and Written Opinion, dated Dec. 13, 2011, for International Application No. PCT/IB2011/053246, 24 pages.
International Search Report and Written Opinion, dated Feb. 26, 2015, for International Application No. PCT/IL2014/050937.
International Search Report and Written Opinion, dated Jul. 20, 2010, for International Application No. PCT/IB2009/055438.
International Search Report and Written Opinion, dated Nov. 26, 2013 for International Application No. PCT/IB2013/000663 filed Feb. 15, 2013.
International Search Report, dated Apr. 5, 2011, for International Application No. PCT/IB2010/054861.
Kantarci et al., Follow-Up of Extracranial Vertebral Artery Stents with Doppler Sonography., Sep. 2006, American Journal of Roentgenology, vol. 187, p. 779-787.
Lal et al., "Duplex ultrasound velocity criteria for the stented carotid artery", Journal of Vascular Surgery, vol. 47, No. 1, pp. 63-73, Jan. 2008.
Larsson et al., "State Diagrams of the Heart—a New Approach to Describing Cardiac Mechanics", Cardiovascular Ultrasound 7:22 (2009).
Liang, Jing et al., Microstrip Patch Antennas on Tunable Electromagnetic Band-Gap Substrates, IEEE Transactions on Antennas and Propagation,vol. 57, No. 6, Jun. 2009.
Lin, J.C. et al., "Microwave Imaging of Cerebral Edema", Proceedings of the IEEE, IEEE, NY, US, vol. 70, No. 5; May 1, 1982, pp. 523-524.
Miura et al. "Time Domain Reflectometry: Measurement of Free Water in Normal Lung and Pulmonary Edema," American Journal of Physiology—Lung Physiology 276:1 (1999), pp. L207-L212.
Notice of Reasons for Rejection, dated Apr. 17, 2015, for JP 2013-520273.
Notice of Reasons for Rejection, dated Apr. 28, 2014, for JP 2012-541588.
Notice of Reasons for Rejection, dated Mar. 31, 2015, for JP 2012-541588.
Partial Supplementary Search Report, dated Oct. 19, 2015, for EP Application No. 13748671.8.
Paulson, Christine N., et al. "Ultra-wideband radar methods and techniques of medical sensing and imaging" Proceedings of Spie, vol. 6007, Nov. 9, 2005, p. 60070L.
Pedersen, P.C., et al., "Microwave Reflection and Transmission Measurements for Pulmonary Diagnosis and Monitoring", IEEE Transactions on Biomedical Engineering, IEEE Service Center, Piscataway, NJ, US, vol. BME-19, No. 1, Jan. 1, 1978; pp. 40-48.
Polhemus, "Fastrak: The Fast and Easy Digital Tracker", USA, 2008.
Ringer et al., Follow-up of Stented Carotid Arteries by Doppler Ultrasound, Sep. 2002, Neurosurgery, vol. 51, No. 3, p. 639-643.
Supplementary European Search Report and European Search Opinion, dated Jun. 13, 2013, for European Application No. 09851811.1.
Supplementary European Search Report and European Search Opinion, dated Mar. 11, 2014, for European Application No. 11809359.1.
Supplementary European Search Report and Search Opinion, dated Dec. 4, 2014, for EP Application No. 10834292.4.
Supplementary European Search Report and Search Opinion, dated Jun. 20, 2013, for European Application No. 09851811.1.
Supplementary European Search Report, dated Mar. 7, 2016, for EP Application No. 13748671.8.
Written Opinion for International Application No. PCT/IB2010/054861 dated Apr. 5, 2011.
Yang, F. et al. "Enhancement of Printed Dipole Antennas Characteristics Using Semi-EBG Ground Plane", Journal of Electromagnetic Waves and Application, U.S., Taylor & Francis, Apr. 3, 2006, vol. 8, pp. 993-1006.

* cited by examiner

IMPLANTABLE RADIO-FREQUENCY SENSOR

CROSS-REFERENCE TO RELATED APPLICATION

This application is a divisional of U.S. patent application No. 13/811,210 (abandoned), filed Mar. 8, 2013, which is a 35 U.S.C. § 371 national stage entry of PCT/IB2011/053244, having an international filing date of Jul. 21, 2011 and claims benefit of U.S. Provisional Patent Application Ser. No. 61/366,173, filed Jul. 21, 2010, the disclosures of which are incorporated herein by reference in their entireties.

FIELD OF THE INVENTION

The present invention relates generally to methods and systems for medical diagnostic measurement and monitoring, and specifically to radio frequency (RF)-based measurement and monitoring of physiological conditions.

BACKGROUND OF THE INVENTION

Radio-frequency (RF) electromagnetic radiation has been used for diagnosis and imaging of body tissues. For example, PCT International Publication WO 2011/067623, which is assigned to the assignee of the present patent application and whose disclosure is incorporated herein by reference, describes diagnostic apparatus that includes an antenna, which directs RF electromagnetic waves into a living body and generates signals responsively to the waves that are scattered from within the body. The signals are processed so as to locate a feature in a blood vessel in the body.

As another example, U.S. Patent Application Publication 2011/0130800, which is assigned to the assignee of the present patent application and whose disclosure is incorporated herein by reference, describes diagnostic apparatus, which includes a plurality of antennas, which are configured to be disposed at different, respective locations on the thorax of a living body. The antennas direct radio frequency (RF) electromagnetic waves from different, respective directions toward the heart in the body and output RF signals responsively to the waves that are scattered from the heart. The RF signals are processed over time so as to provide a multi-dimensional measurement of a movement of the heart.

U.S. Patent Application Publication 2010/0256462 describes a method for monitoring thoracic tissue fluid content by intercepting reflections of electromagnetic (EM) radiation reflected from thoracic tissue of a patient in radiation sessions during a period of at least 24 hours. A change of a dielectric coefficient of the thoracic tissue is detected by analyzing the reflections. PCT International Publication WO 2009/031149 describes a wearable monitoring apparatus comprising at least one transducer configured for delivering EM radiation to internal tissue and intercepting at least one reflection of the EM radiation therefrom. A housing for containing the transducer, along with a reporting unit and a processing unit, is configured to be disposed on the body of an ambulatory user.

The citation of certain references above is intended to provide a general overview of the state of the art and does not constitute an admission that any of the references should be considered prior art against the present patent application.

SUMMARY

Embodiments of the present invention that are described hereinbelow provide implantable devices for measuring tissue characteristics using RF electromagnetic radiation and methods of measurement and monitoring using such devices.

There is therefore provided, in accordance with an embodiment of the present invention, diagnostic apparatus, including a sealed case, which includes a biocompatible material and configured for implantation within a body of a human subject. At least one antenna is configured to be implanted in the body in proximity to a target tissue and to receive radio frequency (RF) electromagnetic waves propagated through the target tissue and to output a signal in response to the received waves. Processing circuitry, which is contained within the case, is coupled to receive and process the signal from the antenna so as to derive and output an indication of a characteristic of the target tissue.

In some embodiments, the at least one antenna is configured to transmit the waves into the body and to receive the transmitted waves following propagation of the waves through the target tissue. In a disclosed embodiment, the at least one antenna is configured to receive the waves after reflection of the waves from a tissue in the body, and the processing circuitry is configured to detect a modulation of the reflection due to at least one of a heartbeat and a respiratory motion of the subject. The modulation may include a cyclical variation due to the heartbeat.

Additionally or alternatively, the apparatus may include a reflector configured for implantation in the body in a location across the target tissue from the case containing the at least one antenna, wherein the reflector serves as the structure for reflecting the waves toward the at least one antenna. The reflector may be a part of an implanted cardiac device (ICD) that is implanted in the body.

In another embodiment, the apparatus includes a transmitter, which is configured to be implanted in the body in a location across the target tissue from the case containing the at least one antenna and to transmit the waves through the target tissue.

In some embodiments, the processing circuitry is configured to process the signal so as to derive a measure of a fluid content of the target tissue. In a disclosed embodiment, the case is configured for implantation in a thorax, and the target tissue is lung tissue. In alternative embodiments, the target tissue is spleen, liver, tongue or palate tissue.

In one embodiment, the indication includes a time trend of the characteristic of the target tissue.

The at least one antenna may include a plurality of antennas. In one embodiment, the processing circuitry is configured to drive the antennas in a multi-static mode so as to spatially resolve the characteristic of the target tissue.

In some embodiments, the at least one antenna is contained inside the case. Typically, the at least one antenna includes a trace printed on a substrate, and wherein the case includes a window, and the antenna is configured to receive the waves through the window. The substrate may be sealed to the case by brazing.

In another embodiment, the at least one antenna is located partially outside the case and is connected to the processing circuitry via a sealed brazing to the case.

In some embodiments, the at least one antenna includes a trace printed on a substrate and a backlobe suppression structure behind the trace. The backlobe suppression structure may be selected from a group of structures consisting of an air cavity and an electromagnetic bandgap (EBG) backing.

The at least one antenna may be selected from a group of antenna types consisting of a spiral antenna, a bowtie antenna, an elliptic bowtie antenna, and a slotted antenna.

In a disclosed embodiment, the processing circuitry is configured to convey the indication of the characteristic via a wireless link to a monitoring station outside the body. Additionally or alternatively, the processing circuitry may be configured to communicate with at least one other implanted device.

The at least one antenna may also be configured to receive electrical energy to power the processing circuitry via an inductive link to a transmitter outside the body. Alternatively, the apparatus includes a power antenna, which is configured to receive electrical energy to power the processing circuitry via an inductive link to a transmitter outside the body.

In a disclosed embodiment, the apparatus includes one or more electrodes on the case for receiving electrical signals within the body. Additionally or alternatively, the apparatus may include a bio-impedance sensor. Further additionally or alternatively, the apparatus includes an implanted cardiac device, which is configured to pace a heart of the subject responsively to the indication provided by the processing circuitry.

There is also provided, in accordance with an embodiment of the present invention, diagnostic apparatus including a radio frequency (RF) reflector, which is configured to be implanted in a body of a human subject in proximity to a target tissue. A diagnostic device is configured to transmit RF electromagnetic waves toward the RF reflector and to receive the waves reflected by the RF reflector through the target tissue, and to process the received waves so as to derive and output an indication of a characteristic of the target tissue.

There is additionally provided, in accordance with an embodiment of the present invention, a diagnostic method, which includes implanting a diagnostic device in proximity to a target tissue in a body of a human subject. The device receives radio frequency (RF) electromagnetic waves propagated through the target tissue and processes the received waves so as to derive an indication of a characteristic of the target tissue.

In a disclosed embodiment, implanting the device includes using an external antenna outside the body to identify an optimal location for implantation of the device.

The present invention will be more fully understood from the following detailed description of the embodiments thereof, taken together with the drawings in which:

DETAILED DESCRIPTION OF EMBODIMENTS

Overview

Figure 1:
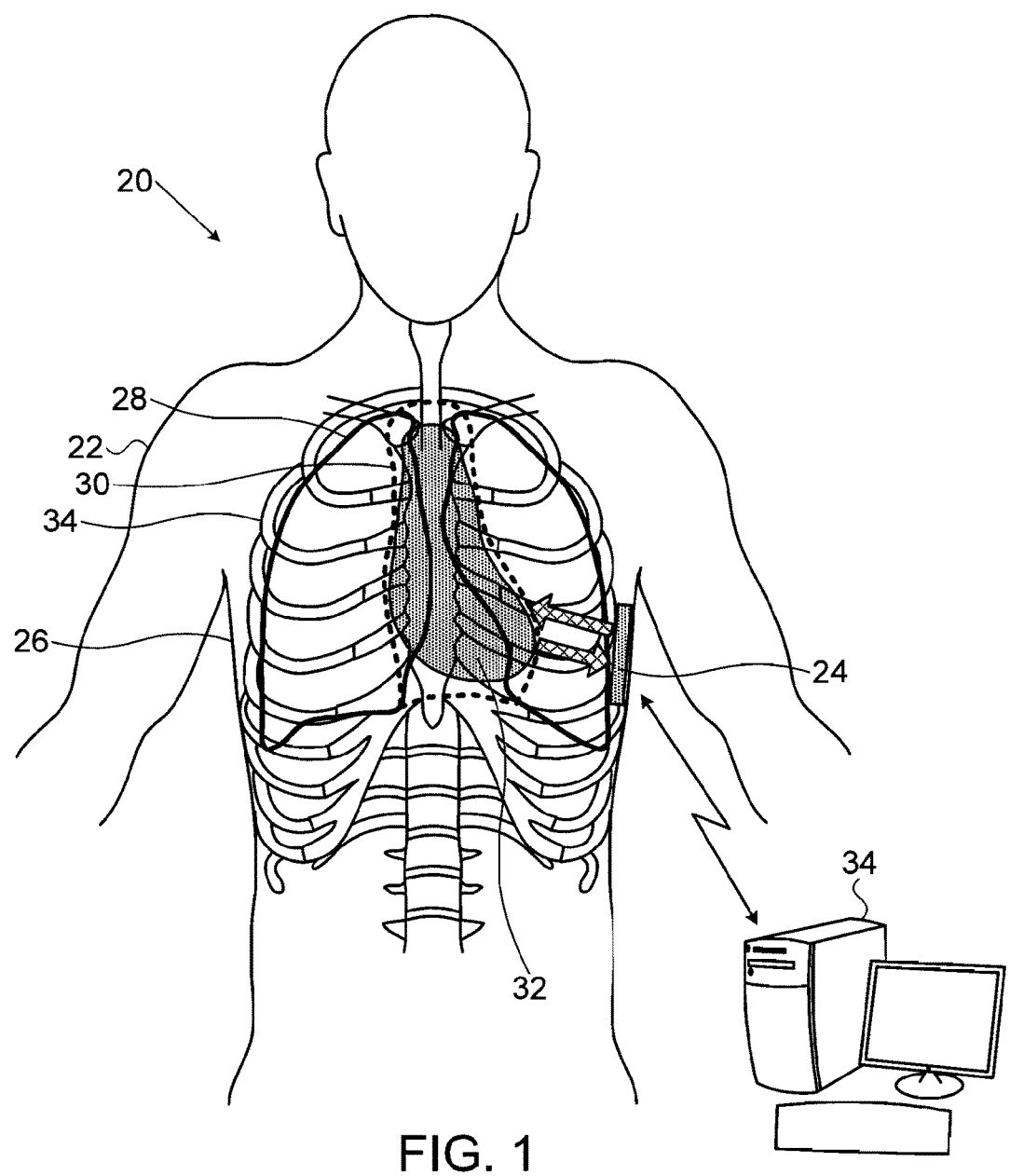
FIG. 1 is a schematic pictorial illustration showing a monitoring system including an implanted RF monitoring device, in accordance with an embodiment of the invention.

A number of chronic medical conditions lead to accumulation of fluid in and around body organs. For example, pulmonary edema is associated with chronic heart failure and other pathologies. As another example, conditions such as kidney failure and certain inflammatory disorders may lead to pericardial effusion. Monitoring such fluid levels in the patient's body over extended periods can be helpful in ongoing risk assessment and adjustment of treatment. Similarly, monitoring accumulation of blood in the splanchnic system can be of medical benefit in assessing fluid status.

Embodiments of the present invention that are described hereinbelow provide implantable devices and methods that can be used for long-term measurement and monitoring of tissue characteristics, such as fluid accumulation in and around body organs. In these embodiments, a diagnostic device comprises at least one antenna and associated processing circuitry, which are contained inside or connected to a sealed case made from a biocompatible material. The device is implanted within the body of a human subject in proximity to a target tissue, such as the lung. The antenna receives radio frequency (RF) electromagnetic waves transmitted through the target tissue. These waves may be transmitted by the antenna itself and then reflected back through the target tissue to the device, or they may be transmitted from another source. The processing circuitry processes the signals that are output by the antenna in order to derive and output an indication of a characteristic of the target tissue, such as the tissue fluid content.

In a disclosed embodiment, the device is implanted in the thorax, adjacent to the lung. The processing circuitry drives the antenna (or antennas) to transmit RF waves through the lung toward the heart, and to receive waves reflected from the heart and transmitted back through the lung. Alternatively, the waves may be reflected back from a dedicated reflector or another reflective object. Further alternatively, the waves may be transmitted through the lung by a separate transmitter, which is implanted in the body in a location across the target tissue from the receiver. The processing circuitry processes the output signals from the antenna in order to derive a measure of the fluid content of the lung. The processing circuitry periodically reports the fluid level by telemetric link to a monitor outside the patient's body, for use by a physician in tracking the patient's condition and making treatment changes as appropriate.

Although the embodiments described herein are directed specifically to monitoring of fluid levels in the lungs, the principles of the present invention may similarly be applied in other monitoring applications. For example, implanted devices of the types described herein may be used, mutatis mutandis, in monitoring pericardial fluid levels. As another example, such a device may be used to monitor bladder fill level and/or muscle properties in patients suffering from urinary disorders, in order to provide an alert when the bladder should be emptied. In other embodiments, such devices may be used in long-term monitoring of fluid levels in the brain, tongue, palate or spleen, as well as in body extremities, such as the thighs. More generally, the devices and methods described herein may be adapted for use in substantially any long-term diagnostic application in which tissue characteristics are evaluated using RF electromagnetic waves, including not only fluid monitoring but also imaging applications, as well.

System Description

Figure 2:
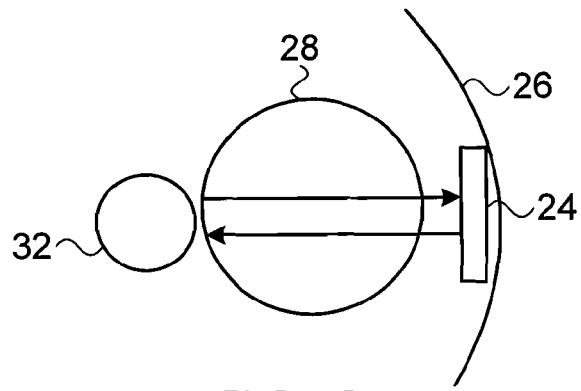
FIG. 2 is a schematic sectional view of a RF monitoring device implanted in a human body, in accordance with an embodiment of the invention.

Reference is now made to FIGS. 1 and 2, which schematically illustrate a RF-based monitoring system 20, in accordance with an embodiment of the invention. FIG. 1 is a pictorial illustration, showing a RF monitoring device 24 implanted in a thorax 26 of a patient 22, while FIG. 2 is a sectional view taken through the body, showing the relation of device 24 to organs in the thorax. Device 24, which is typically similar in shape and size to a conventional implanted cardiac device (ICD), such as a pacemaker, is implanted below the patient's skin adjacent to ribs 34 and transmits and receives RF electromagnetic waves through target tissue, such as a lung 28, as indicated by arrows in the figure.

Figure 5:
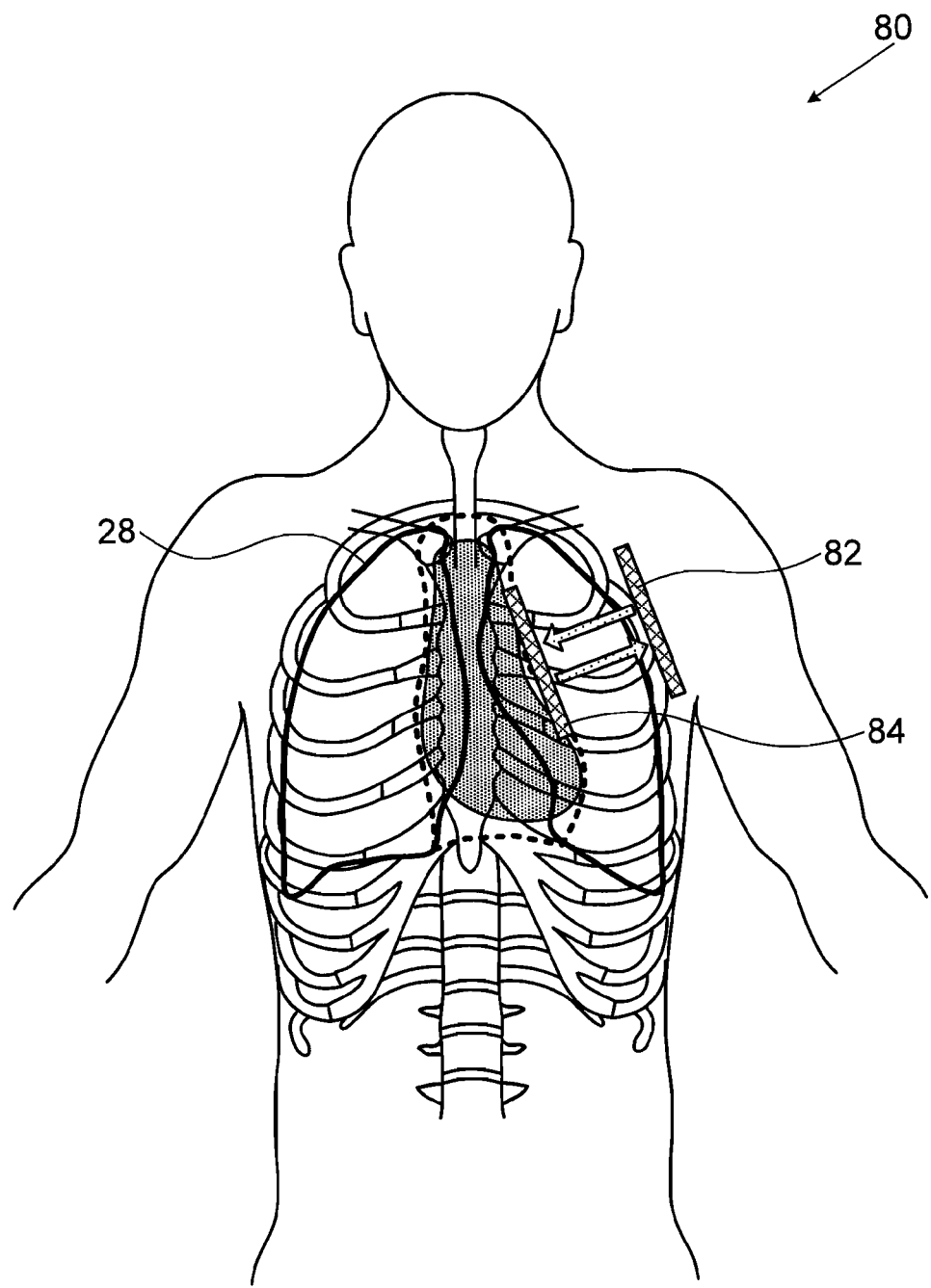
FIG. 5 is a schematic pictorial illustration showing a RF monitoring device implanted in a human body, in accordance with another embodiment of the invention.
Figure 6A:
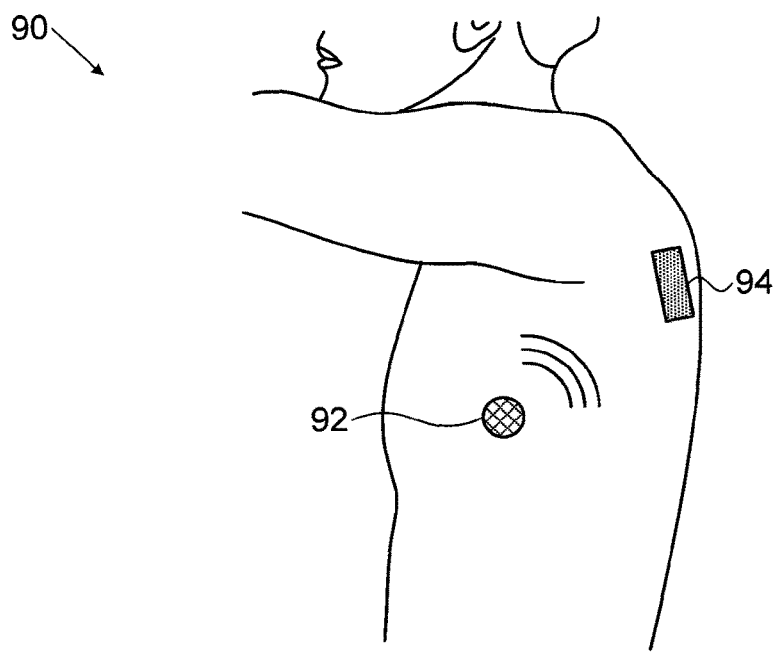
FIGS. 6A and 6B are schematic pictorial illustrations, in side and front views respectively, showing a RF monitoring device implanted in a human body, in accordance with a further embodiment of the invention.
Figure 6B:
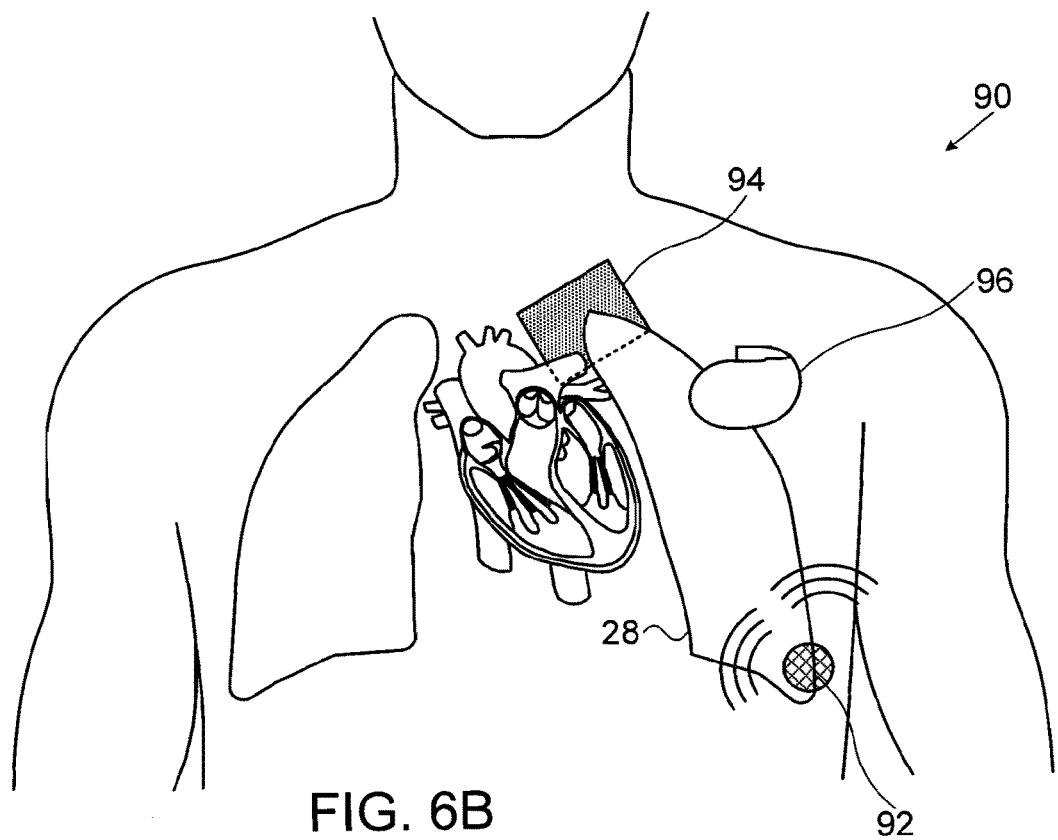

In the pictured example, device 24 is implanted in the axillary region using a minimally-invasive procedure. The waves transmitted by device 24 pass through lung 28 and mediastinum 30, reflect back from heart 32 through lung 28, and are then received and detected by device 24. Alternatively, the device may be implanted in other suitable locations, such as the infra-mammary or dorsal regions of thorax 26. An external antenna may be used during implantation to choose an optimal antenna location, based upon which the surgeon implants device 24 and its implanted antenna at the location giving the best signal. In some alternative embodiments, as shown in FIGS. 5, 6A and 6B, for example, the monitoring device may be used in conjunction with an implanted reflector, instead of or in addition to sensing reflections from the heart.

RF monitoring device 24 processes the received RF waves to derive an indication of tissue characteristics, such as tissue fluid content. Device 24 collects these indications over time and periodically transmits the data to a telemetry station 34, typically via a suitable short-range wireless link. Station 34 typically comprises a general-purpose computer with suitable communication circuits and software, and may be located in a clinic or hospital or in the home or workplace of patient 22. Station 34 may also be configured to program device 24 over the wireless link, as well as to provide RF energy to recharge the battery in device 24, as described below.

Figure 3:
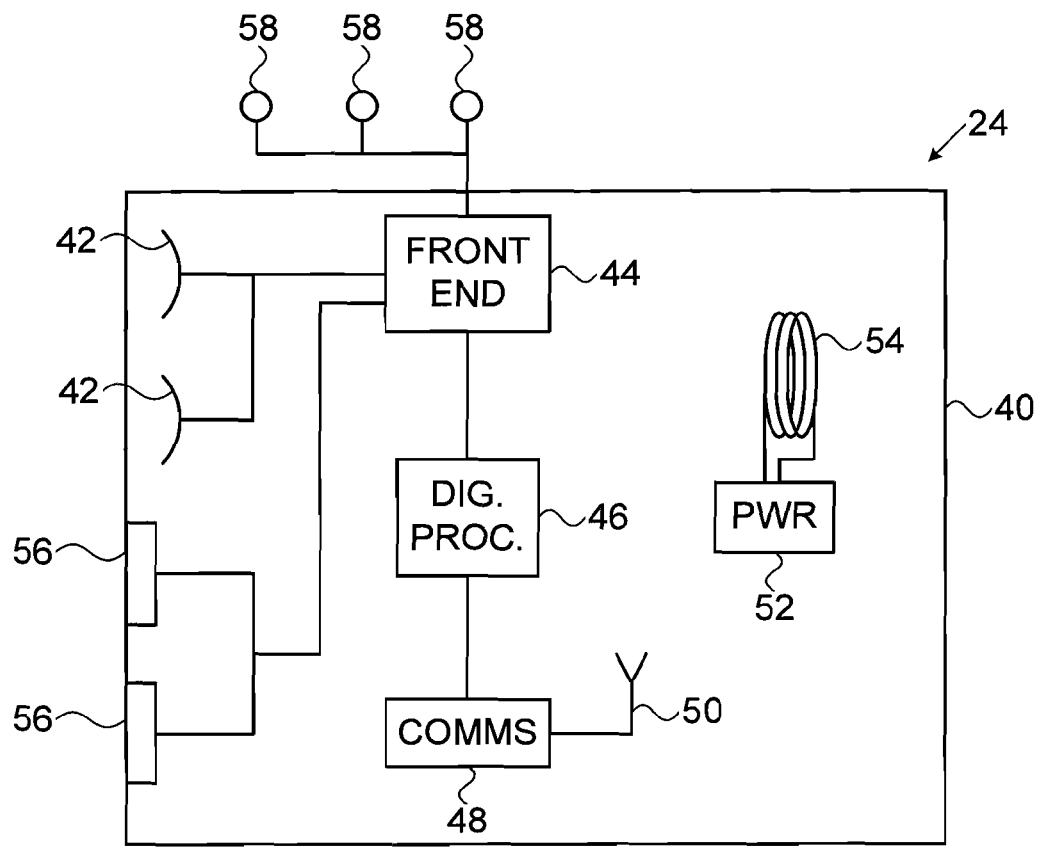
FIG. 3 is a block diagram that schematically shows functional components of an implantable RF monitoring device, in accordance with an embodiment of the invention.

FIG. 3 is a block diagram that schematically shows functional elements of RF monitoring device 24, in accordance with an embodiment of the invention. The elements of device 24 are contained in a sealed case 40, comprising a suitable biocompatible material, such as titanium or stainless steel. The case may be coated with a tissue-growth inducing material, as is known in the art. Case 40 contains, inter alia, processing circuitry including a RF front end 44 and a digital processing circuit 46. Front end 44 drives one or more antennas 42 to emit RF waves through lung 28. The front end receives and processes the signals that are output by antennas 42 in response to the reflected waves and outputs a digitized indication of the amplitude and phase of the signals to digital processing circuit 46. Typically, for high resolution in the presence of background noise, front end 44 and circuit 46 apply coherent methods of signal processing to correlate the reflected signals with the transmitted signals, but alternatively non-coherent processing methods may be used.

In one embodiment, front end 44 generates signals at multiple different frequencies for exciting the transmitting antennas. Device 24 may operate in an ultra-wide-band (UWB) mode, in which the signals are spread over a wide range of frequencies, such as from about 500 MHz to about 2.5 GHz (although higher and lower frequencies outside this range may also be used). UWB transmission and detection techniques of this sort are described, for example, in the above-mentioned PCT International Publication WO 2011/067623 and U.S. Patent Application Publication 2011/0130800. The UWB signal provides the frequency-domain equivalent of a very short pulse in the time domain and can thus be used for measuring the range of a reflecting spot in the body with high accuracy. The UWB signal can be transmitted as a short pulse or as a train of narrowband signals that together constitute a wideband signal, or other waveforms used in radar pulse compression (such as chirped, stepped-frequency, or phase-coded pulses). Use of these sorts of waveforms in making measurements inside the body is described in the above-mentioned publications and may similarly be applied, mutatis mutandis, in system 20.

Digital processing circuit 46 measures the time delay for RF waves to travel from antenna 42 to heart 32 via lung 28 and back to the antenna. The waves reflected from the heart can be identified based on the modulation, typically comprising a cyclical change, of the resulting signal during a heartbeat. The short-term time cyclical variation of the delay from antenna to heart and back can also be used to measure heart movement, while long-term variation is indicative of changes in the pulmonary fluid level. Additionally or alternatively, electrodes 56, which may be built into case 40 or mounted externally, may measure an electrocardiogram (ECG) signal for correlation with the actual heart movement. Further additionally or alternatively, circuit 46 may detect modulation of the waves due to respiratory motion.

Further additionally or alternatively, device may comprise other sensors 58, either in case 40 or connected to it externally. Sensors 58 may measure, for example, bio-impedance, fluid content, temperature, salinity, or motion (of the heart, lungs, or entire body) and may be useful in filling out the picture of fluid status that is provided by RF measurement.

As the RF waves pass through body tissue, such as lung 28, the group velocity of the waves will vary as a function of the fluid content of the tissue. Generally speaking, the higher the fluid content, the greater will be the dielectric constant of the tissue, and hence the lower the velocity. Equivalently, fluid in the lungs can be considered to increase the RF path length of the waves, defined by the length of time required for the waves to pass through the tissue and back to device 24. The result of this decrease in velocity or increase in RF path length is that the delay of the reflected waves will increase as the fluid content of lungs 28 increases. Digital processing circuit 46 measures this delay periodically and/or on command in order to compute an indication of the lung's fluid content. Typically, circuit 46 comprises a memory (not shown), which stores the computed values.

In addition to or alternatively to measuring the RF path length or delay, digital processing circuit may measure other signal characteristics, such as the amplitude of the reflected signals from the transition layer between ribs 34 and lung 28. The amplitude of this reflection is typically stronger and differently shaped in patients suffering from pulmonary edema in comparison to healthier subjects. The signal amplitude and shape may also be fitted parametrically to a stratified model of the various tissues traversed by the RF waves, wherein the fit parameters include the fluid content.

Additionally or alternatively, circuit 46 may compute other parameters relating to tissue characteristics, such as the volume, shape, physical properties, locations and/or movement of structures in the path of the RF waves within the body. For example, the RF waves and signal processing carried out in front end 44 and circuit 46 may be adjusted to measure pericardial fluid content within mediastinum 30. As another example, antennas 42 can be driven in a multi-static configuration to measure the electromagnetic properties of different sub-volumes within thorax 26, and thus provide data that are spatially resolved in two or three dimensions. Such multi-static techniques (using extracorporeal antennas) are described, for example, in the above-mentioned WO 2011/067623 and US 2011/0130800, which also describe digital signal processing methods that can be used to compute the complex dielectric constants for the individual sub-volumes.

A communication interface 48 transmits and receives data to and from telemetry station 34 (FIG. 1) via a communication antenna 50. The transmitted data typically comprise the indications of tissue characteristics that have been computed over time and stored by digital processing circuit 46. These indications may include statistical parameters computed by circuit 46 over the tissue measurement results, such as time trend parameters of the measured fluid level. Alternatively or additionally, the indications of tissue characteristics may include raw data collected from front end 44, and communication interface 48 may transmit data either intermittently or continuously as they are measured. Further alternatively or additionally, interface 48 may communicate with other implanted diagnostic and/or therapeutic devices, such as an intravascular pressure sensor or an ICD, or with non-invasive monitoring devices, such as a bio-impedance measurement device.

A power source 52 supplies operating power to the circuits of device 24. Power source 52 typically comprises an energy storage component, such as a single-use or rechargeable battery. In the case of a rechargeable storage component, power source 52 may be coupled to a power antenna 54, which receives RF power from a suitable power transmission antenna (not shown) outside the body. Alternatively, one or more of antennas 42 may additionally receive this RF power, instead of or in addition to power antenna 54. The power transmission antenna may comprise, for example, a coil, which is positioned outside thorax 26 in proximity to device 24 and provides power to antenna 54 by magnetic induction. The power transmission coil may be placed under a mattress on which the patient lies, or it may be worn as a vest, a bra or a necklace, for example. Power source 52 rectifies the received power in order to charge its energy storage component.

Figure 4A:
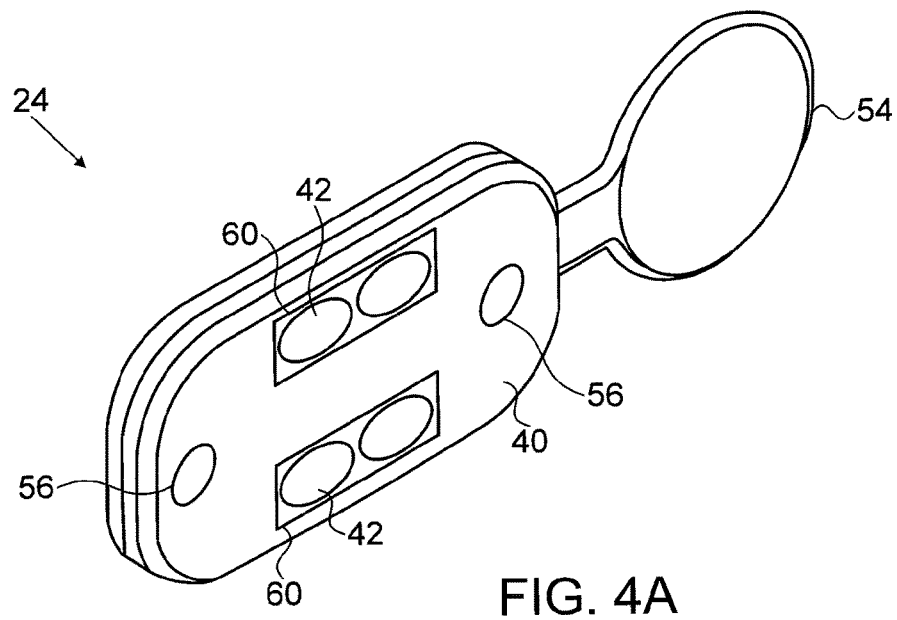
FIG. 4A is a schematic pictorial illustration of an implantable RF monitoring device, in accordance with an embodiment of the invention.
Figure 4B:
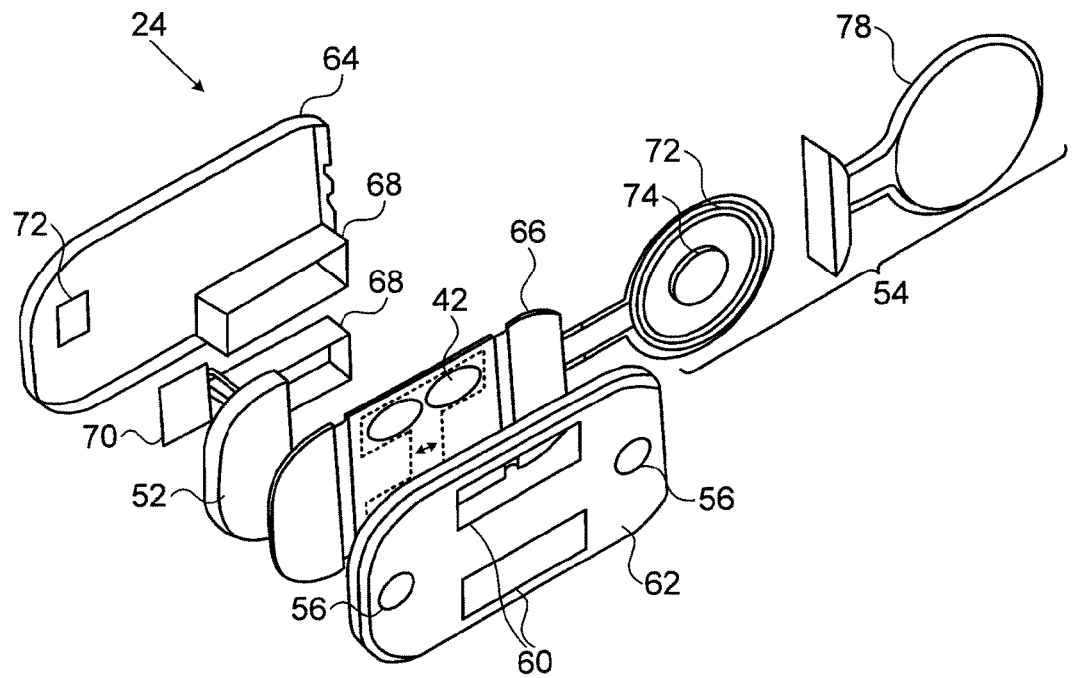
FIG. 4B is a schematic exploded view of the device of FIG. 4A.

FIG. 4A is a schematic pictorial illustration of RF monitoring device 24, in accordance with an embodiment of the invention, while FIG. 4B shows a schematic exploded view of the device of FIG. 4A. Case 40 comprises front and rear covers 62, 64, typically comprising titanium. Antennas 42 are printed, using hard gold or another suitable biocompatible conductor, on a main circuit board 66, which typically comprises a biocompatible ceramic substrate with brazing to enable it to be hermetically sealed against covers 62 and 64. Board 66 also has pads and conductors for mounting and connecting the components (not shown) of front end 44, processing circuit 46, and communication interface 48. These components are typically embodied in one or more integrated circuits, as are known in the art. Front cover 62 comprises windows 60 containing antennas 42, which are sealed by bonding the perimeters of the windows to brazing surrounding the antennas on board 66.

Antennas 42 in this example each comprise a pair of printed conductive loops with a center feed, in an elliptic bowtie configuration. For enhanced efficiency and directionality, antennas 42 are backed by conductive air-filled cavities 68 on the side of board 66 opposite windows 60. Cavity antennas of this sort (in an extracorporeal configuration) are described, for example, in the above-mentioned PCT International Publication WO 2011/067623. Alternatively, device 24 may comprise any other suitable type of antenna, such as a spiral, bowtie, or slotted antenna, with a cavity, electromagnetic bandgap (EBG) backing, or no backing.

Power antenna 54 comprises a coil 72 with a magnetic or ferritic core 74, covered by a non-conductive biocompatible cover 78. Coil 72 is connected via feed-throughs between covers 62 and 64 to power source 52. Cover 78 typically comprises a suitable biocompatible plastic or other dielectric material, such as silicone molded over coil 72 and core 74. Coil 72 may also serve as communication antenna 50. Alternatively, a separate communication antenna 70 may be connected to board 66 and positioned to transmit and receive communication signals through a window 72 in cover 64. As still another alternative, one or both of antennas 42 may serve as the communication antenna (although in this case it may be preferable that the antenna not have a cavity or other backing in order to strengthen the backlobe radiation transmitted by the antenna out of the body).

As noted earlier, device 24 comprises electrodes 56, which are shown in FIGS. 4A and 4B as external elements on cover 62. The ECG signals sensed by these electrodes may be used not only in synchronizing the measurements of RF reflections to the patient's heartbeat, but also as a diagnostic indicator in and of themselves, which is processed and stored by circuit 46. This diagnostic indicator can then be used, for example, to detect cardiac arrhythmias, in a manner similar to a Holter monitor. Alternatively or additionally, device 24 can comprise sensors for other sorts of intra-body clinical measurements, such as temperature, blood pressure, and/or blood oxidation, thereby broadening the usefulness and improving the diagnostic accuracy of system 20.

Alternative Embodiments

FIG. 5 is a schematic pictorial illustration of a monitoring system 80 comprising a RF monitoring device 82 implanted in a human body, in accordance with another embodiment of the invention. Device 82 is similar in structure and function to device 24, as described above, but in this embodiment, device 82 operates in conjunction with an internally-placed reflector 84 on the opposite side of the patient's lung, as shown in the figure, rather than relying on reflections from the heart. The use of a dedicated reflector strengthens the reflected waves that are received by device 82 and provides a constant physical path length to which the measured RF path length can be compared. Alternative placements of the monitoring device and reflector are shown in FIGS. 6A and 6B. As yet another alternative, the RF reflector may be positioned outside the patient's body.

Reflector 84 may be a passive structure made of biocompatible conducting material, or it may comprise one or more active components, which can be modulated to enhance signal extraction by device 82. The modulation of this reflector can be triggered and powered externally by means of a magnetic pulse source or a low-frequency electromagnetic wave. As another alternative, an internal active or passive reflector of this sort can be used in conjunction with an external RF transmitter/receiver, in place of device 82.

In an alternative embodiment, reflector 84 may be replaced by a RF transmitter, which transmits RF waves through the lung to device 82. In this case, device 82 may comprise only a RF receiver (together with the processing circuitry and other components shown in FIG. 3). As still another alternative, transmit/receive devices on opposite sides of the heart may each transmit RF waves and receive the RF waves transmitted by the counterpart device.

FIGS. 6A and 6B are schematic pictorial illustrations, in side and front views respectively, showing a system 90 in which a RF monitoring device 92 is implanted in a human body, in accordance with a further embodiment of the invention. In this embodiment, device 92 is similar in structure and function to device 24, but is implanted in an infra-mammary location and operates in conjunction with a reflector 94 in a dorsal location, between the fourth and sixth ribs, for example. Alternatively, the locations of device 92 and reflector 94 may be reversed.

FIG. 6B also shows an ICD 96, which may be used in conjunction with device 92 or integrated with device 92. For example, device 92 and pacemaker 96 may share a power source and/or communication circuits for communicating with station 34 outside the body. Device 92 and ICD 96 may even be contained in the same case, which may be implanted, for example, in the infra-mammary region. The measurements provided by device 92, particularly with regard to the level of pulmonary fluid accumulation, may be used as an input in controlling the pacing of the heart by ICD 96.

ICD 96 may alternatively serve as the reflector for device 92, in place of reflector 94. In this case, the ICD may simply be configured as a passive reflector, or it may comprise a modulated reflector, as described above.

Figure 7:
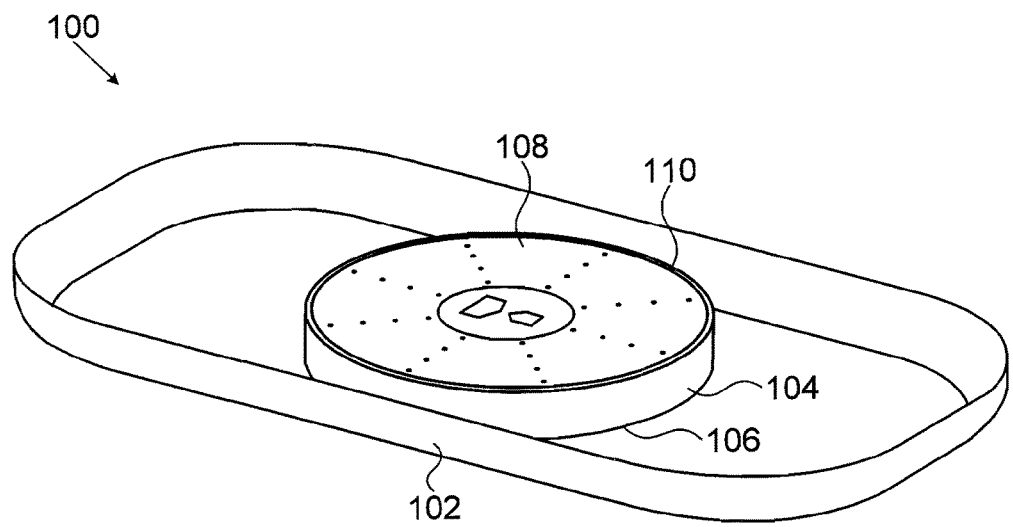
FIG. 7 is a schematic pictorial illustration of a part of a RF monitoring device, in accordance with another embodiment of the present invention.

FIG. 7 is a schematic pictorial illustration of a part of a RF monitoring device 100, in accordance with another embodiment of the present invention. This figure shows the internal side of case 102 of device 100, to which a cylindrical antenna support 104 is attached, by laser welding along a seam 106, for example. A substrate 108 of the antenna is mounted on support 104. Substrate 108 typically comprises a ceramic material, such as a low-temperature co-fired ceramic (LTCC), for example, Dupont 951LTCC. Substrate 108 comprises a metal coating around its perimeter, and is brazed to support 104 (as well as to the overlying front side of case 102, which is not shown in this figure) using a titanium ring 110 and a suitable filler material. The brazing serves the dual purposes of electromagnetically sealing the antenna to its backing and mechanically sealing the substrate to the case.

Figure 8:
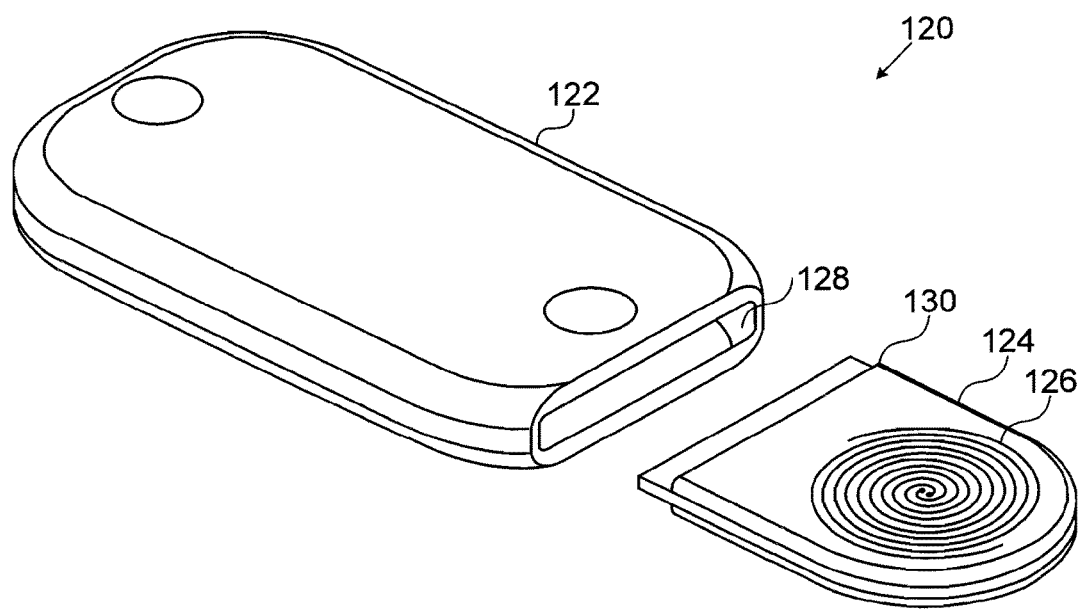
FIG. 8 is a schematic, partly-exploded view of a RF monitoring device, in accordance with yet another embodiment of the present invention.

FIG. 8 is a schematic, partly-exploded view of a RF monitoring device 120, in accordance with yet another embodiment of the present invention. In this embodiment, an antenna 124 is attached externally to a sealed case 122 of device 120. Antenna 124 in this example comprises a conductive spiral 126, but this sort of external configuration in equally applicable to other antenna types. Antenna 124 is inserted into a slot 128 in case 122, and an edge 130 of the antenna is then sealed to case 122 by brazing, for example. The antenna is thus partially inside and partially outside the case, with sealed RF connections from the circuits inside the case to the outer antenna using printed electrical traces.

Figure 9:
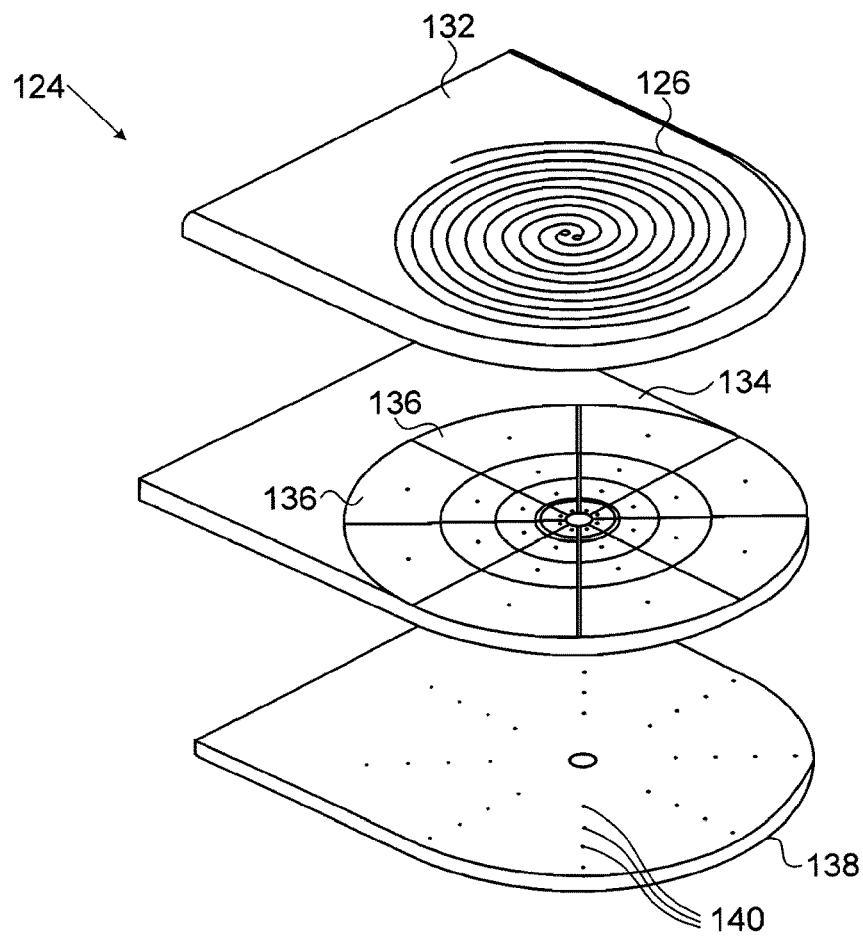
FIG. 9 is a schematic exploded view of an antenna used in the embodiment of FIG. 8.

FIG. 9 is a schematic exploded view of antenna 124, in accordance with an embodiment of the present invention. Antenna 124 comprises a stack of three layers, each on a respective ceramic substrate 132, 134, 138. Spiral 126 is printed on the upper layer. An EBG structure 136 is printed on the middle layer, serving as a backing for spiral 126, with EBG elements of different sizes corresponding to the different frequencies radiated by different areas of the spiral. The lower layer serves as a ground plane, with vias 140 passing through all the layers of antenna 124. The vias are connected via leads (not shown) on substrate 138 to the circuits inside case 122. The two central vias provide the signals for exciting spiral 126.

Figure 10:
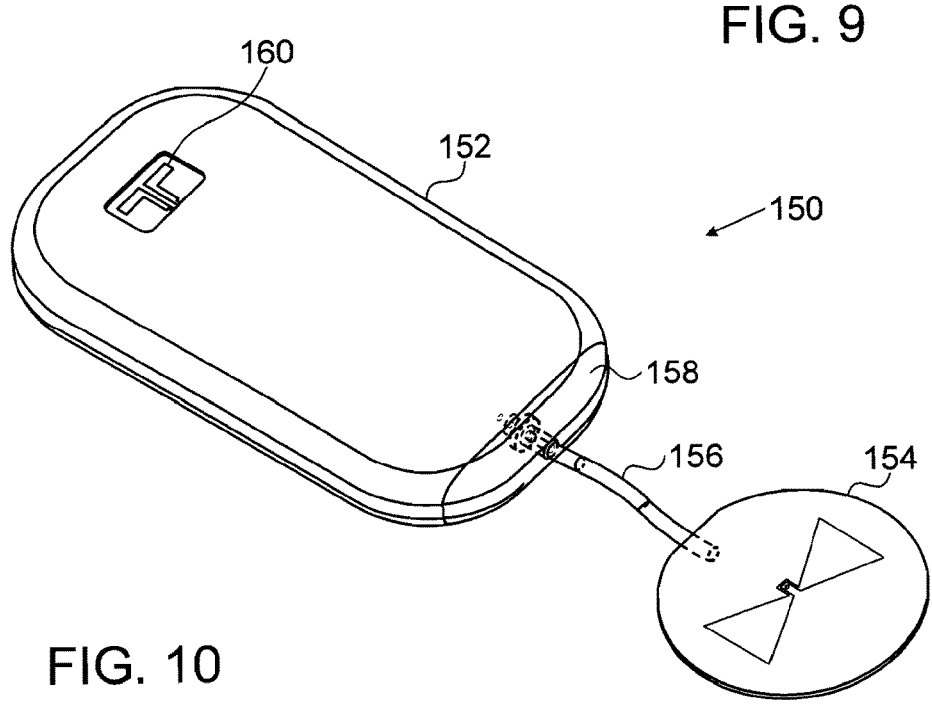
FIG. 10 is a schematic pictorial illustration of a RF monitoring device, in accordance with an additional embodiment of the present invention.

FIG. 10 is a schematic pictorial illustration of a RF monitoring device 150, in accordance with an additional embodiment of the present invention. Here a bowtie antenna 154 is connected by a coaxial cable 156 to circuits inside a case 152. The cable and case are sealed by a feedthrough in a header 158, which may comprise a suitable epoxy and/or polyurethane. Device 150 in this embodiment also has a communication antenna 160, as described above.

As noted earlier, although the embodiments shown in the figures relate specifically to measurement of the fluid content of the lungs, the principles of the present invention may similarly be applied in monitoring of other organs, such as the heart, bladder, tongue, palate, spleen, brain, or body extremities. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A diagnostic apparatus, comprising:
    a sealed case, comprising a biocompatible material and configured for implantation within a body;
    a first antenna and a second antenna, each antenna configured to:
        be implanted in the body in proximity to a target tissue,
        generate and transmit radio frequency (RF) electromagnetic waves through the target tissue to the other antenna, and
        output a signal in response to RF waves received from the other antenna; and
    processing circuitry, which is contained within the case and is configured to receive and process the signal from each antenna so as to derive and output an indication of a characteristic of the target tissue.

2. The apparatus according to claim 1, wherein a characteristic of the target tissue includes a measure of a fluid content of the target tissue.

3. The apparatus according to claim 2, wherein the measure of the fluid content of the target tissue comprises a measure of a change in a level of the fluid content of the target tissue.

4. The apparatus according to claim 1, wherein the processing circuitry is further configured to determine a modulation of the signal from each antenna.

5. The apparatus according to claim 1, further comprising RF front-end circuitry contained within the housing and configured to drive at least one of the first antenna and the second antenna to emit RF waves.

6. The apparatus according to claim 5, wherein the front end circuitry generates signals at multiple different frequencies when driving at least one of the first antenna and the second antenna.

7. The apparatus according to claim 1, wherein at least one of the first antenna and the second antenna comprises a trace printed on a substrate and a backlobe suppression structure behind the trace.

8. The apparatus according to claim 7, wherein the backlobe suppression structure comprises at least one of an air cavity, a plastic cavity, or an electromagnetic bandgap (EBG) backing.

9. The apparatus according to claim 1, wherein the processing circuitry is configured to process the signal to determine at least one of a heartbeat and a respiratory motion of the body.

10. The apparatus according to claim 1, further comprising a power antenna, configured to receive electrical energy to power the processing circuitry via an inductive link.

11. The apparatus according to claim 1, wherein at least one of the first antenna and the second antenna comprises a spiral antenna, a bowtie antenna, an elliptic bowtie antenna, or a slotted antenna.

12. The apparatus according to claim 1, wherein at least one of the first antenna and the second antenna is located partially outside the case and is connected to the processing circuitry via a sealed brazing to the case.

13. The apparatus according to claim 1, wherein at least one of the first antenna and the second antenna is contained inside the case.

14. The apparatus according to claim 13, wherein at least one of the first antenna and the second antenna comprises a trace printed on a substrate, and wherein the case comprises a window, and the antenna is configured to receive the waves through the window.

15. The apparatus according to claim 1, further comprising one or more ECG electrodes configured to measure an ECG of the body, and correlate the characteristic of the target tissue with the ECG of the body.

16. A diagnostic apparatus, comprising:
   a sealed case, comprising a biocompatible material and configured for implantation within a body of a patient;
   a first antenna and a second antenna, each antenna configured to:
      be implanted in the body in proximity to a lung of the patient,
      generate and transmit radio frequency (RF) electromagnetic waves through the lung of the patient to the other antenna, and
      output a signal in response to RF waves received from the other antenna; and
   processing circuitry, which is contained within the case and is configured to receive and process the signal from each antenna so as to derive and output
   an indication of a measure of a change in a level of the fluid content in the lung of the patient; and
   at least one of a heart beat of the patient and a respiratory motion of the patient.

17. The apparatus according to claim 16, further comprising one or more ECG electrodes configured to measure an ECG of the patient, and correlate at least the heart beat of the patient with the ECG of the patient.

18. The apparatus according to claim 16, wherein at least one of the first antenna and the second antenna comprises a trace printed on a substrate and a backlobe suppression structure behind the trace.

19. The apparatus according to claim 18, wherein at least one of the first antenna and the second antenna comprises a spiral antenna, a bowtie antenna, an elliptic bowtie antenna, or a slotted antenna.

* * * * *